(12) United States Patent
Everett (10) Patent No.: US 9,739,853 B2
(45) Date of Patent: Aug. 22, 2017

(54) PATIENT SUPPORT TABLE TOP FILLER

(71) Applicant: KONINKLIJKE PHILIPS N.V., Eindhoven (NL)

(72) Inventor: Dennis K Everett, Seven Hills, OH (US)

(73) Assignee: KONINKLIJKE PHILIPS N.V., Eindhoven (NL)

(*) Notice: Subject to any disclaimer, the term of this patent is extended or adjusted under 35 U.S.C. 154(b) by 641 days.

(21) Appl. No.: 14/347,651

(22) PCT Filed: Sep. 20, 2012

(86) PCT No.: PCT/IB2012/054988
§ 371 (c)(1),
(2) Date: Mar. 27, 2014

(87) PCT Pub. No.: WO2013/046097
PCT Pub. Date: Apr. 4, 2013

(65) Prior Publication Data
US 2014/0232406 A1      Aug. 21, 2014

Related U.S. Application Data

(60) Provisional application No. 61/540,133, filed on Sep. 28, 2011.

(51) Int. Cl.
*G01R 33/30* (2006.01)
*A61G 13/12* (2006.01)
(Continued)

(52) U.S. Cl.
CPC ............. *G01R 33/30* (2013.01); *A47C 27/14* (2013.01); *A61B 5/0555* (2013.01);
(Continued)

(58) Field of Classification Search
CPC .. G01R 33/30; G01R 33/34046; A47C 27/14; A61B 5/0555; A61G 13/121; A61G 13/1285
See application file for complete search history.

(56) References Cited

U.S. PATENT DOCUMENTS 3,742,528 A * 7/1973 Munch ................. A47C 27/148
                                                              5/648
3,947,686 A * 3/1976 Cooper ................ A61B 6/0442
                                                              378/209

(Continued)

*Primary Examiner* — G. M. Hyder (57) ABSTRACT

When imaging a patient using a magnetic resonance (MR) imager, it is desirable to locate an radio frequency (RF) head coil at a position lower than the flat table top patient surface in order to optimize the geometry of the patient anatomy and the RF coil. A flat table top is provided for an MR patient support table (10) that includes a pocket or recessed portion (50) that accepts an RF head coil (14), thereby optimizing imaging geometry. When the RF coil is not mated to the recessed portion of the table (10) a filler insert (20) is mated therewith. This allows an operator to use the table top without the filler insert to position a neurovascular coil at an optimized location below the table top surface for brain imaging, as well as to convert the patient support table back to a completely flat top by removing the coil and installing the flat surface filler insert for additional positioning requirements. The filler insert feature allows for therapy planning using magnetic resonance with optimized image quality in a radiation therapy treatment environment.

15 Claims, 8 Drawing Sheets

(51) Int. Cl.
  *A61B 5/055*   (2006.01)
  *G01R 33/34*   (2006.01)
  *A47C 27/14*   (2006.01)

(52) U.S. Cl.
  CPC ....... *A61G 13/121* (2013.01); *A61G 13/1285* (2013.01); *G01R 33/34046* (2013.01)

(56) References Cited

U.S. PATENT DOCUMENTS

| | | |
|---|---|---|
| 6,377,830 B1 | 4/2002 | Carrozzi |
| 7,603,164 B2 | 10/2009 | Uematsu |
| 7,869,857 B2 | 1/2011 | Satragno |
| 2007/0191706 A1 | 8/2007 | Calderon |
| 2008/0191696 A1 | 8/2008 | Van Der Burgt |
| 2009/0211027 A1* | 8/2009 | Dimmer .................. A61B 5/06 5/601 |
| 2009/0306494 A1* | 12/2009 | Scarth .................. A61B 5/0555 600/411 |
| 2009/0306495 A1 | 12/2009 | Scarth |
| 2010/0102814 A1 | 4/2010 | Satragno |
| 2011/0113555 A1 | 5/2011 | Smith |

* cited by examiner

PATIENT SUPPORT TABLE TOP FILLER

CROSS-REFERENCE TO PRIOR APPLICATIONS

This application is the U.S. National Phase application under 35 U.S.C. §371 of International Application No. PCT/IB2012/054988, filed on Sep. 20, 2012, which claims the benefit of U.S. Provisional Patent Application No. 61/540,133, filed on Sep. 28, 2011. These applications are hereby incorporated by reference herein.

The present application finds particular application in medical imaging systems, particularly involving patient support systems. However, it will be appreciated that the described technique may also find application in other diagnostic systems, other imaging systems, or the like.

In medical diagnostic imaging, an issue arises in the transfer of an imaging subject to and from the imaging apparatus. In many cases, the subject is disabled and unable to assist in the transfer process. In some instances it is important to preserve patient position.

Typically, the patient is placed on a wheeled patient couch or other movable subject support that is adapted to mechanically dock with the medical diagnostic magnetic resonance imaging scanner or other imaging apparatus. In one known approach, a locking mechanism that locks the couch to the imaging apparatus is triggered by operation of a brake pedal of the patient couch. Once connected, a conveyor belt of the imaging apparatus is linked with a patient supporting pallet or top of the patient couch, and the patient and pallet are transported into a magnet bore of the magnetic resonance imaging apparatus for imaging.

After the imaging session is complete, the patient and pallet are transported back and reconnected to the patient couch base. The operator disconnects the conveyor belt of the imaging apparatus from the patient couch. The brake pedal is released, which also unlocks the patient couch from the subject support, and the patient couch is wheeled away.

Medical imaging systems, such as magnetic resonance (MR) scanners, transmission computed tomography (CT) scanners, positron emission tomography (PET) scanners, gamma cameras for single-photon emission computed tomography (SPECT), and so forth are powerful tools in detecting physiological manifestations of diseases caused by hazardous contagions, exposure to radioactivity or toxic substances, and so forth. For example, such imaging techniques can detect malignant tumors or other abnormalities that may be indicative of infection or disease. Medical imaging techniques can be applied periodically (for example on an hourly, daily, weekly, or other basis) to image live human or animal subjects so as to track the progression of physiological response to the disease or to exposure to a radioactive or toxic agent. Techniques such as multi-nuclear MR spectroscopy can track metabolic changes associated with the disease progression. These medical imaging-based diagnostics are merely illustrative examples.

The present application relates to new and improved systems and methods that facilitate improving scintillator crystal performance, which overcome the above-referenced problems and others.

In accordance with one aspect, a patient support system for a magnetic resonance imaging (MRI) device includes a patient support table having a recessed portion, and a radio frequency (RF) head coil assembly that has a bottom surface shape that is complementary to and mates with the recessed portion of the patient support table. The system further includes a filler insert that has a flat top surface and a bottom surface having a contoured shape that is complementary to and mates with the recessed portion of the patient support table. The filler insert is installed on the patient table support at times when the RF head coil assembly is not installed on the on the patient table support.

In accordance with another aspect, a patient support table insert comprises a flat top surface that, when the table insert is mated with a recessed portion of a patient support table, lays flush with a top surface of the patient support table. The insert further comprises a bottom surface that is contoured in a manner such that the shape of the bottom surface is complementary to a shape of the recessed portion of the patient support table such that the bottom surface of the insert fits into and mates with the recessed portion of the patient support table.

In accordance with another aspect, a method of maintaining a flat surface on a patient support table when an insertable radio frequency (RF) head coil is not installed therein comprises maintaining a filler insert in a recessed portion of a patient support table. When a patient is to be scanned using an RF head coil, the filler insert is removed and the RF head coil is installed into the recessed portion of the patient support table. When the patient scan is complete, the RF head coil is removed from the recessed portion of the patient support table and the filler insert is re-installed into the recessed portion of the patient support table.

One advantage is that patient comfort is improved.

Another advantage resides in facilitating sanitization of the patient support.

Still further advantages of the subject innovation will be appreciated by those of ordinary skill in the art upon reading and understanding the following detailed description.

The innovation may take form in various components and arrangements of components, and in various steps and arrangements of steps. The drawings are provided for purposes of illustrating various aspects and are not to be construed as limiting the invention.

Figure 1:
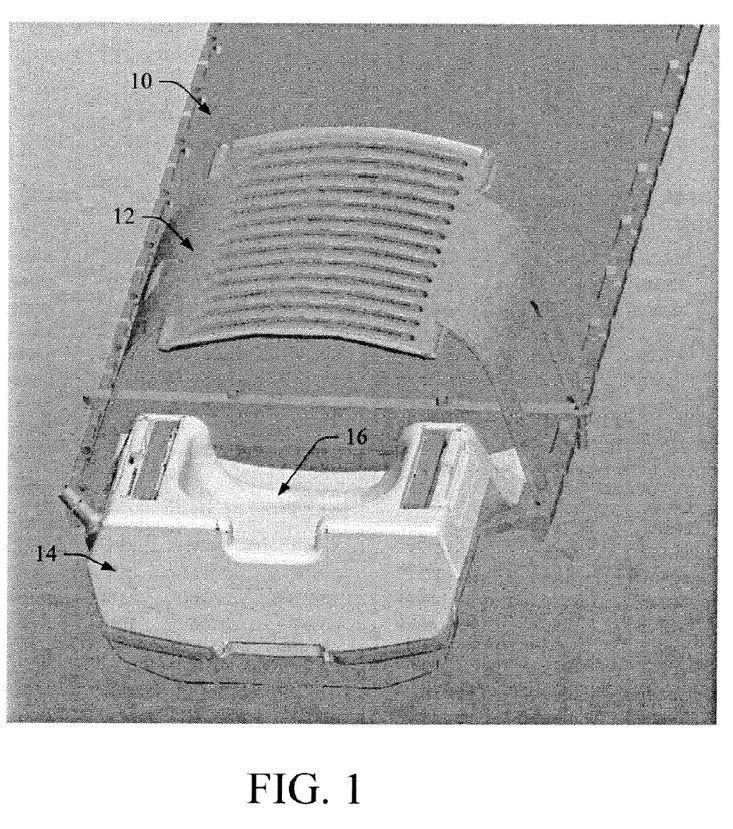
FIG. 1 illustrates a patient support table to which an MR coil is coupled for imaging a patient's body.

For an integrated MR and/or linear accelerator therapy radiation therapy (RT) system, it is desirable to have a flat table top with locating features for associated patient positioning devices. To obtain the optimum image quality, specific RF coils are used, such as the head coil of FIG. 1. It is also desirable to locate such coils at a position lower than the flat table top patient surface in order to optimize the geometry of the patient anatomy and the RF coil. It is possible to create a flat table top for an MR patient support pallet that includes a pocket or recessed portion that accepts an RF head coil, thereby optimizing imaging geometry. Accordingly, FIG. 1 illustrates a flat table top with a filler insert that allows the operator to use the top without the filler insert to position a neurovascular coil at an optimized location below the table top surface for brain imaging, and which also converts back to a completely flat top by removing the coil and installing the flat surface filler insert for additional positioning requirements. The filler insert feature allows for therapy planning using magnetic resonance with optimized image quality in a radiation therapy treatment environment.

FIG. 1 illustrates a patient support table 10 to which an MR coil 12 is coupled for imaging a patient's body. The table is translated linearly into a bore of a magnetic resonance (MR) scanner (not shown) in order to image the patient, and then translated out of the bore when imaging is complete. The table 10 also comprises a recessed portion (not visible in FIG. 1) in which a radio frequency (RF) coil 14 for imaging the patient's head is inserted, such that the patient's head is positioned in a recess 16 in the RF coil 14. The bottom of the RF head coil unit has a surface shape that is congruent to the recessed portion of the patient support table 10. In one embodiment, the RF coil is a neurovascular (NV) coil.

Figure 2:
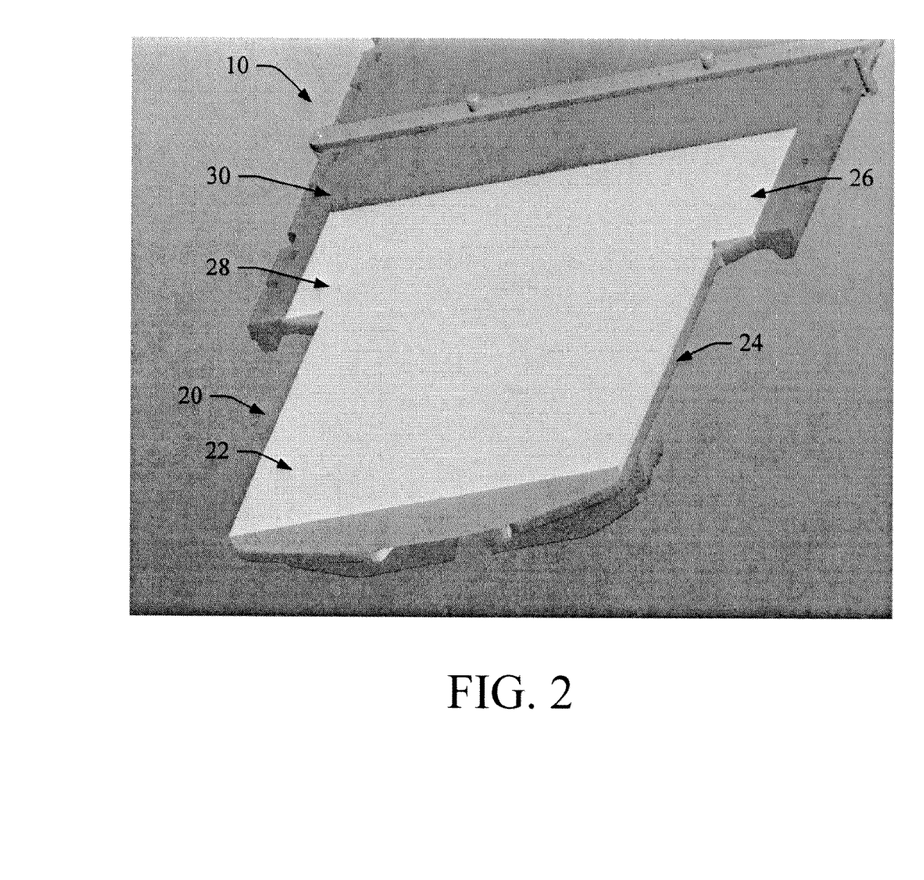
FIG. 2 is an illustration of the patient support table with a table filler insert installed therein.

FIG. 2 is an illustration of the patient support table 10 with a table filler insert 20 installed therein. The table filler insert has a bottom surface similar or identical to the bottom surface of the RF head coil that mates with the recessed portion of the table 10 (not visible in FIG. 2). In this manner, the tale filler insert 20 mates with the table 10 to fill in the recessed portion that normally receives the RF head coil (FIG. 1). However, the top surface of the table filler insert 20 is flat to provide surface that is flush with the rest of the support table with the RF head coil is not in use. The table filler insert 20 includes a "head" portion 22 that mates with a portion 24 of the table where a patient's head is positioned. The insert 20 also includes extensions 26, 28 that fill in a recessed portion of an upper body portion 30 of the table 10 that supports the patient's shoulders. The flat top surface of the insert 20 is easily cleaned or sanitized and prevents contamination of the table surface to which it is mated.

Figure 3:
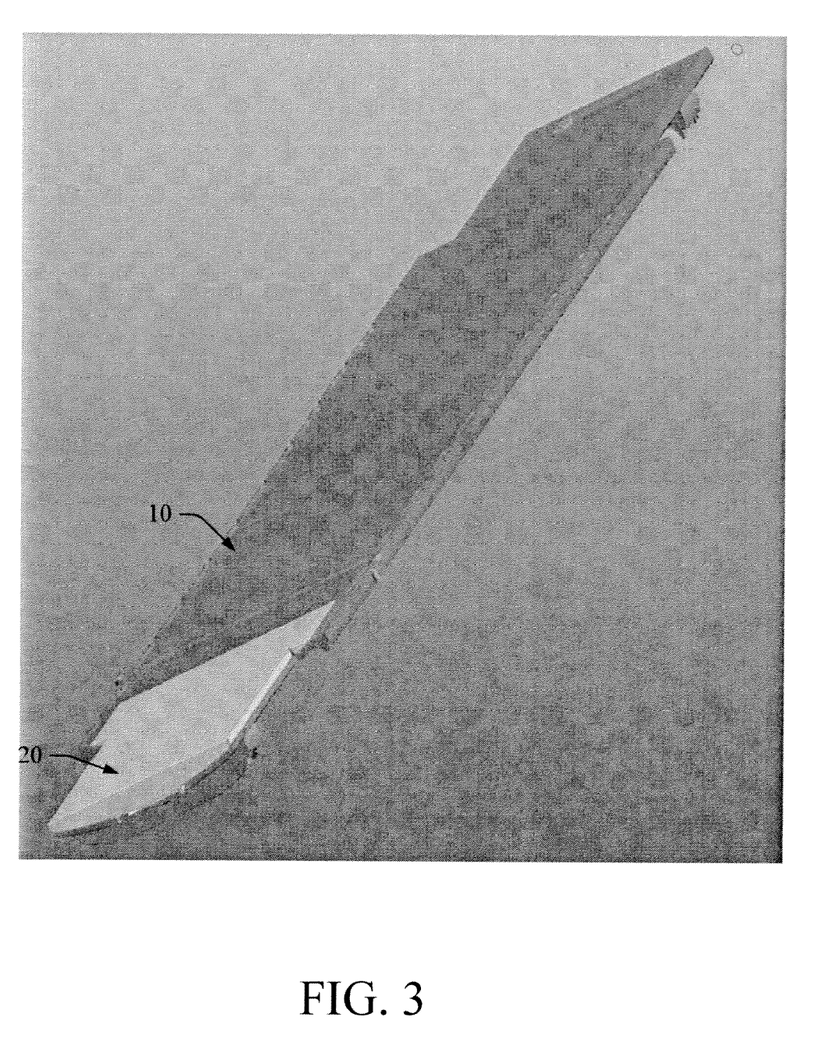
FIG. 3 illustrates another view of the patient support table with the flat-topped filler insert that mates with and fills in a recessed portion that normally receives an RF head coil.

FIG. 3 illustrates another view of the patient support table 10 with the flat-topped filler insert 20 that mates with and fills in a recessed portion that normally receives an RF head coil assembly such as a neurovascular coil assembly or the like.

Figure 4:
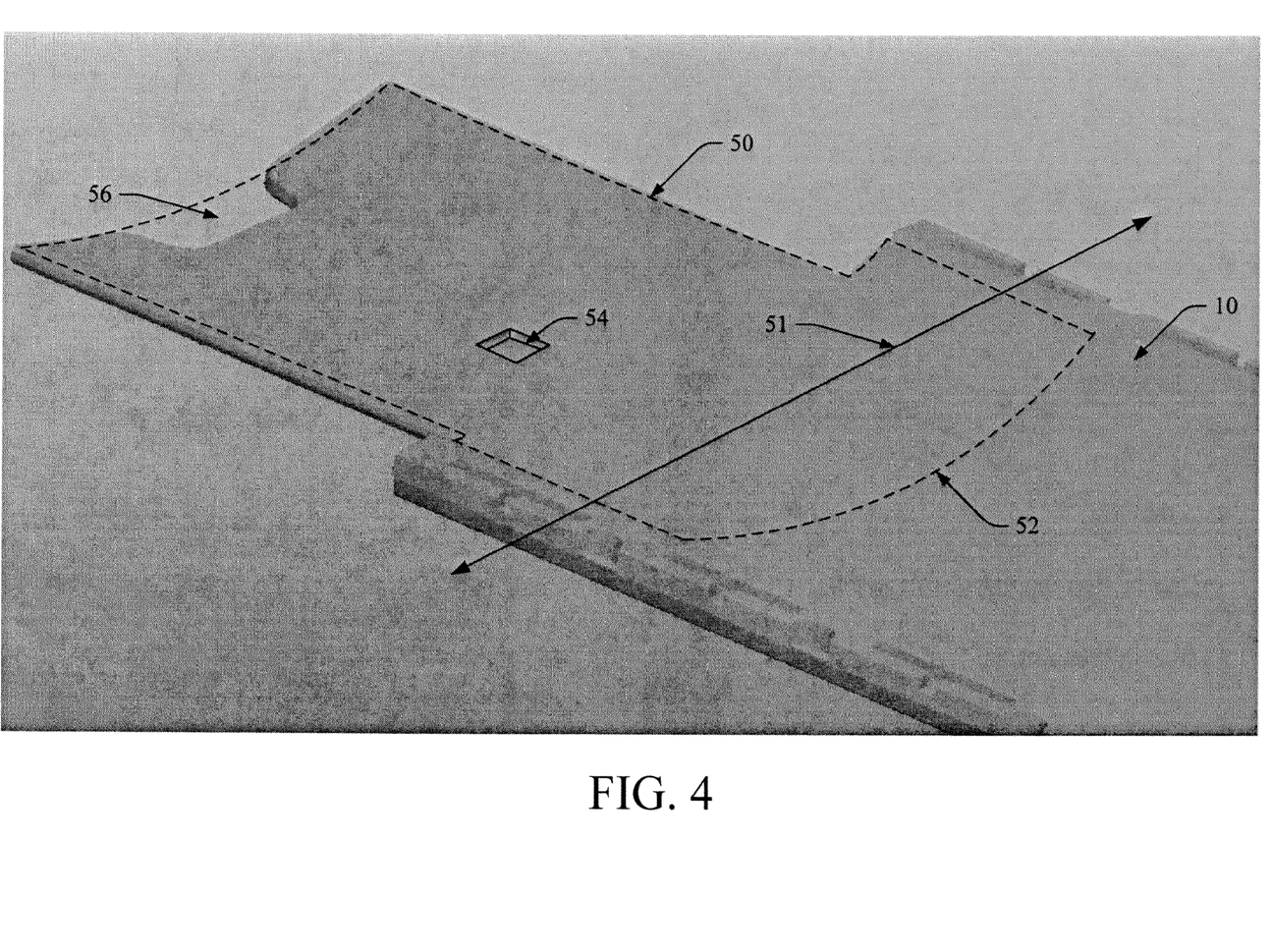
FIG. 4 is an illustration of the patient support table, showing the recessed portion.

FIG. 4 is an illustration of the patient support table 10, showing the recessed portion 50. The recessed portion 50 is concave from one side to the other across a lateral axis 51 across the table, wherein the concave contour 52 has a radius of curvature that is complementary to a convex radius of curvature of the bottoms of the NV coil assembly and the filler insert, both of which mate with recessed portion 50 of the table 10. The recessed portion 50 of the table 10 also includes a central keying recess 54 that receives a complementary protrusion or feature on the bottom of the NV coil assembly and the filler insert when either item is mated with the table 10. Additionally, the recessed portion 50 of the table 10 includes an anterior keying recess 56 that receives a complementary protrusion or feature on the bottom of each of the bottom of the NV coil assembly and the filler insert when either item is mated with the table 10. The central keying feature and the anterior keying feature align the NV coil assembly and the filler insert in the recessed portion 50 of the table 10 when either item is mated with the table 10.

Figure 5:
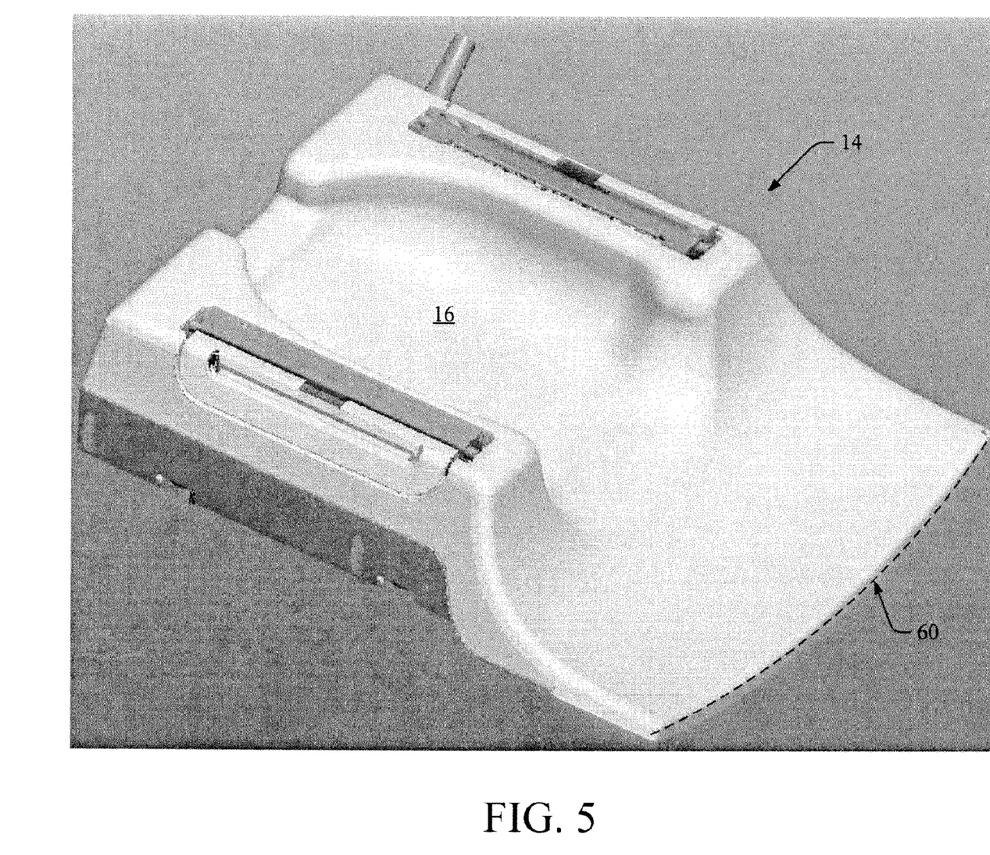
FIG. 5 is an illustration of the NV coil assembly, which includes a recess that receives a patient's head.

FIG. 5 is an illustration of the NV coil assembly 14, which includes a recess 16 that receives a patient's head. The bottom of the NV coil assembly 14 has a convex contour 60 with a radius of curvature that is complementary to the concave radius of curvature (FIG. 4) of the recessed portion 50 patient support table 10. The coil assembly also includes a central keying feature (not visible in FIG. 5) and an anterior keying feature (not visible in FIG. 5) on its bottom surface. The keying features align with central and anterior recesses in the recessed portion 50 of the table 10 to align the coil assembly to the table.

Figure 6:
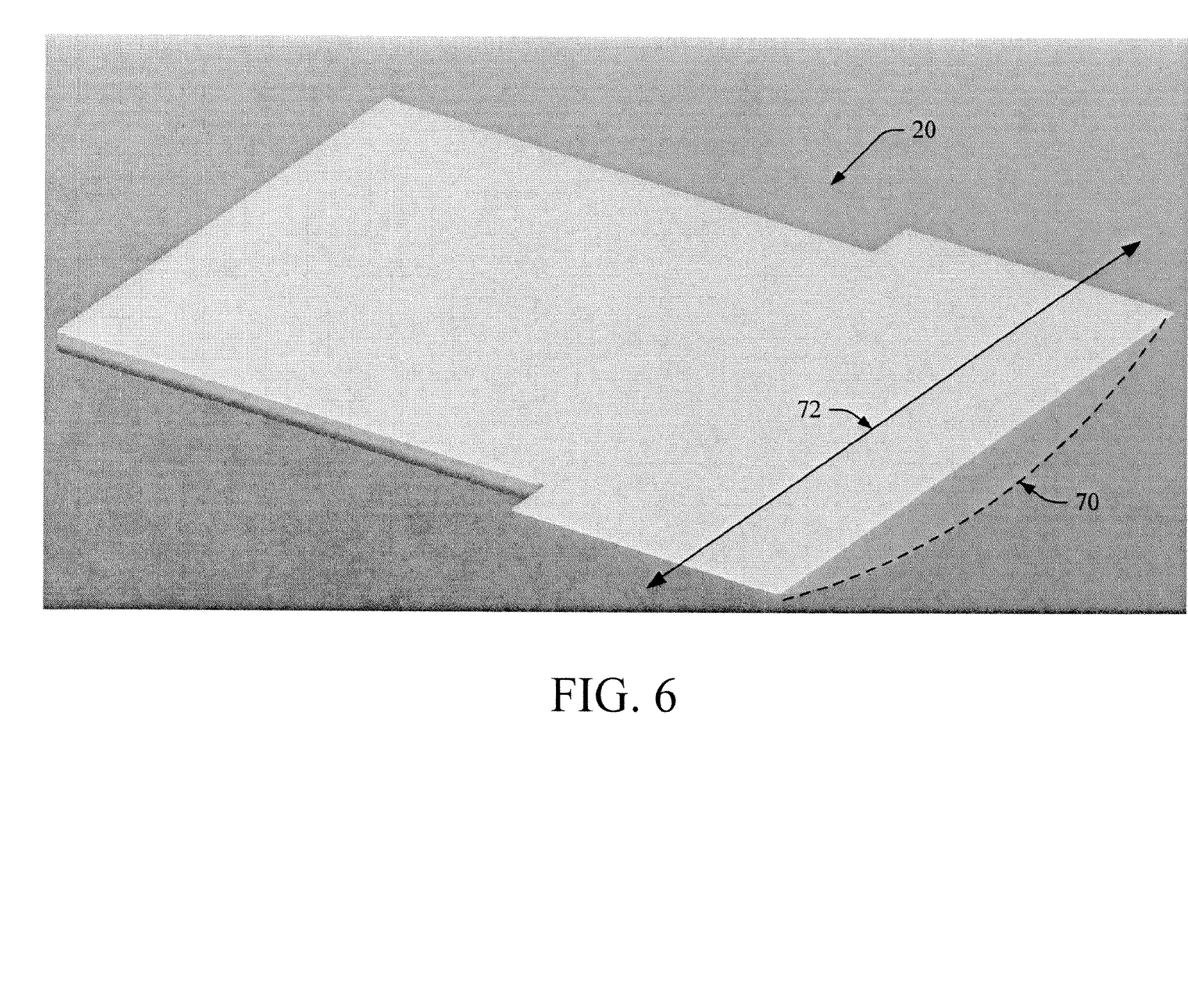
FIG. 6 is an illustration of the filler insert wherein the bottom surface of the insert has a radius of curvature that is similar or identical to the radius of curvature of the NV coil assembly and complementary to the radius of curvature of the recessed portion of the table.

FIG. 6 is an illustration of the filler insert 20. The bottom surface of the insert 20 has a convex contour 70 with a radius of curvature that is similar or identical to the radius of curvature (FIG. 5) of the NV coil assembly 14 and complementary to the radius of curvature of the recessed portion 50 of the table 10 (FIG. 4). The convex contour 70 of the bottom surface spans a lateral axis 72 across the width of the insert 20. In one embodiment, the insert comprises a foam core (e.g., Styrofoam or some other suitable lightweight foam material) and a Kevlar™ (or other suitable aramid or para-aramid material) covering or shell. However, other materials may be employed to manufacture the insert 20.

Figures 7A, 7C, 7D:
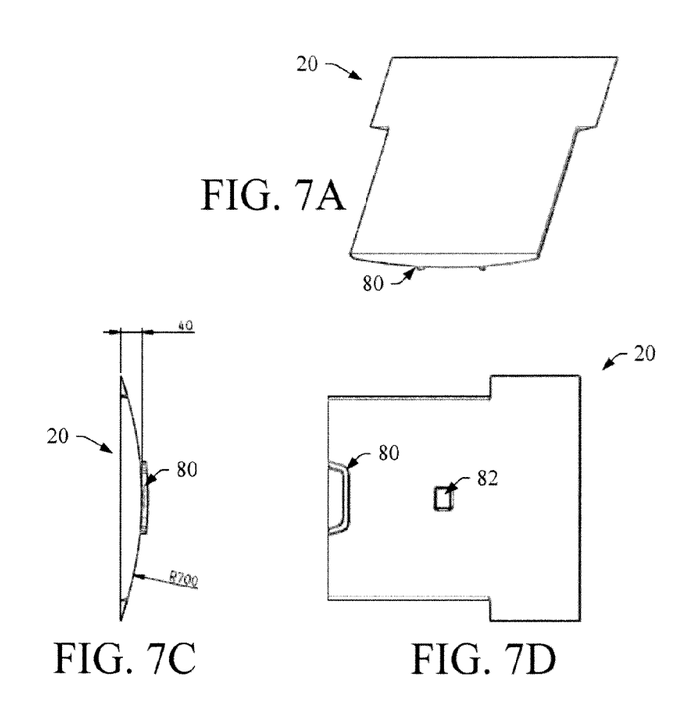
FIG. 7A is an elevated perspective view of the filler insert, in which the anterior keying feature is visible on the curved bottom side of the insert.
FIG. 7C illustrates a side view of the filler insert, in which the anterior keying feature is visible.
FIG. 7D is a bottom view of the filler insert, which includes the anterior keying feature that mates with an anterior keying recess in the table.

FIGS. 7A-7D illustrate the filler insert 20 from various vantage points. FIG. 7A is an elevated perspective view of the filler insert 20, in which the anterior keying feature 80 is visible on the curved bottom side of the insert 20.

Figure 7B:
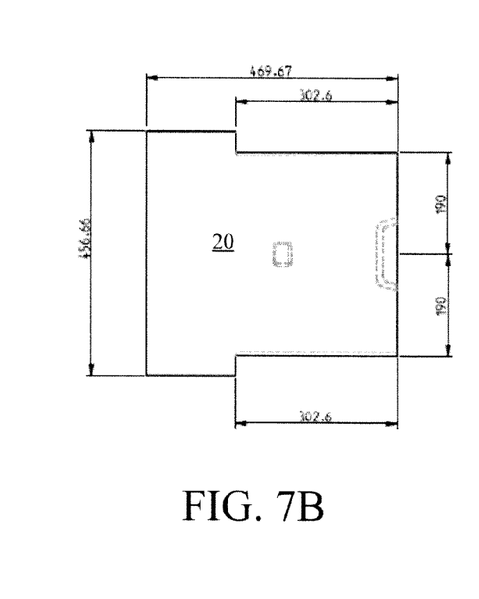
FIG. 7B is a top-down view of the insert.

FIG. 7B is a top-down view of the insert 20. In one embodiment, the insert 20 is mated with a Philips Ingenia patient support table. In this example, the insert has an overall length of approximately 470 mm, with the extensions 26, 28 accounting for approximately 167 mm and the head portion 22 of the insert 20 being approximately 303 mm in length. The width of the insert along the head portion or anterior edge is approximately 380 mm, and the width along the posterior edge of the insert 20 is approximately 157 mm. In other embodiments, the overall width of the insert 20 is in the range of approximately 300 mm-500 mm, and the overall length of the insert is in the range of approximately 400 mm-600 mm. It will be understood that the foregoing dimensions are exemplary in nature and provided only for illustrative purposes and are not intended to limit the scope of the described innovation and/or the claims presented herein. Rather, the dimensions of the filler insert 20 may be any suitable dimensions for a filler insert that has a bottom surface of a shape that is complementary to a recessed portion of a table support and having a flat top surface such that the insert is flush with the table top when mated with the table.

FIG. 7C illustrates a side view of the filler insert 20, in which the anterior keying feature 80 is visible. In the example in which the filler insert is designed for mating with a Philips Ingenia table, the filler insert has a thickness of approximately 40 mm, and the bottom surface of the filler insert 20 has a radius of curvature of approximately 700 mm. In other embodiments, the thickness of the of the insert 20 is in the range of 20 mm-100 mm, 30 mm-50 mm, or some other suitable thickness or range thereof. It will be understood that the foregoing dimensions are exemplary in nature and provided only for illustrative purposes and are not intended to limit the scope of the described innovation and/or the claims presented herein. Rather, the dimensions of the filler insert 20 may be any suitable dimensions for a filler insert that has a bottom surface of a shape that is complementary to a recessed portion of a table support and having a flat top surface such that the insert is flush with the table top when mated with the table.

FIG. 7D is a bottom view of the filler insert 20. The filler insert 20 includes the anterior keying feature 80, which mates with an anterior keying recess 56 in the table 10 (FIG. 4). The insert 20 also includes a central keying feature 82 that is positioned approximately centrally on the bottom surface of the insert 20 and mates with the central keying recess in the recessed portion 50 of the patient support table 10 (FIG. 5).

Figure 8:
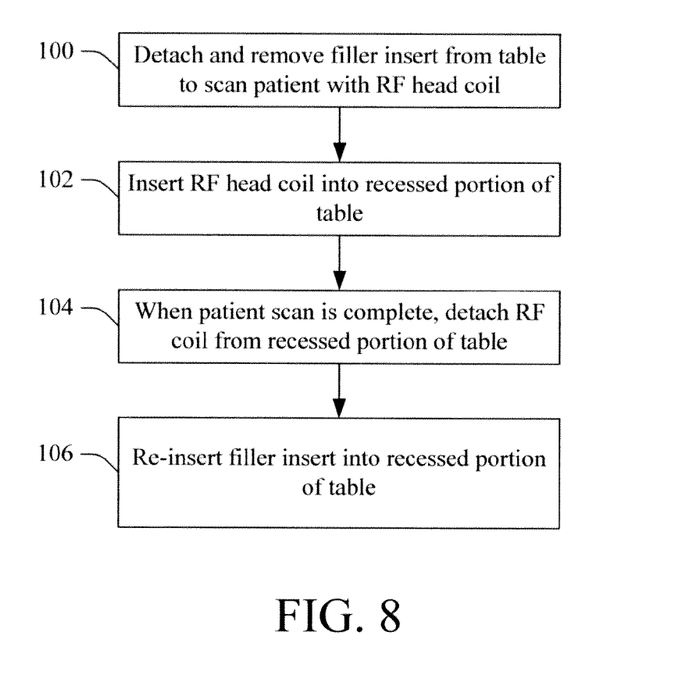
FIG. 8 illustrates a method of employing the filler insert described herein.

FIG. 8 illustrates a method of using the described filler insert, in accordance with one or more aspects described herein. At 100, the filler insert is detached and removed from the recessed portion of the patient support table. At 102, the RF coil is attached to the recessed portion of the table for scanning a patient. Once the patient scan is complete, the RF coil is detached and removed from the patient support table, at 104. At 106, the filler insert is re-inserted into the recessed portion for the patient support table to provide a flat surface for scanning a patient when no RF head coil is required. In one embodiment, the method is employed using a Philips Ingenia patient support table and a Philips NV coil assembly such as the coil assembly shown in FIGS. 1 and 5.

The innovation has been described with reference to several embodiments. Modifications and alterations may occur to others upon reading and understanding the preceding detailed description. It is intended that the innovation be construed as including all such modifications and alterations insofar as they come within the scope of the appended claims or the equivalents thereof

Having thus described the preferred embodiments, invention is now claimed to be:

1. A patient support system for a magnetic resonance imaging (MRI) device, including:
    a patient support table having a recessed portion;
    a radio frequency head coil assembly that has a bottom surface shape that is complementary to and mates with the recessed portion of the patient support table; and
    a filler insert that has a flat top surface and a bottom surface having a contoured shape that is complementary to and mates with the recessed portion of the patient support table;
    wherein the filler insert is installed on the patient table support at times when the RF head coil assembly is not installed on the on the patient table support;
    wherein the recessed portion of the patient support table includes a central keying recess that is positioned approximately at a center of the recessed portion, and an anterior keying recess that is positioned along an anterior edge of the recessed portion; and
    wherein the filler insert includes an anterior keying feature that mates with the anterior keying recess and a central keying feature that mates with the central keying recess to align and secure the filler insert in place on the patient support table.

2. The system according to claim 1, wherein the recessed portion of the patient support table has a concave contour having a radius of curvature that is complementary to a convex contour radius of curvature of the bottom surface of the RF coil assembly and to a convex contour radius of curvature of the bottom surface of the filler insert.

3. The system according to claim 2, wherein the radius of curvature of each of the recessed portion of the patient support table, the bottom surface of the RF head coil assembly, and the bottom surface of the filler insert is approximately 700 mm.

4. The system according to claim 1, wherein filler insert comprises a foam core and a shell that comprises a para-aramid material.

5. The system according to claim 1, wherein the RF head coil assembly is a neurovascular coil assembly.

6. A patient support table filler insert comprising:
    a flat top surface that, when the filler insert is mated with a recessed portion of a patient support table, lays flush with a top surface of the patient support table; and
    a bottom surface that is contoured in a manner such that the shape of the bottom surface is complementary to a shape of the recessed portion of the patient support table such that the bottom surface of the insert fits into and mates with the recessed portion of the patient support table;
    wherein the filler insert includes an anterior keying feature that mates with an anterior keying recess in the recessed portion of the patient support table and a central keying feature that mates with a central keying recess in the recessed portion of the patient support table to align and secure the filler insert in place on the patient support table.

7. The table insert according to claim 6, wherein the bottom surface of the insert has a convex contour that spans a lateral axis through the insert and mates with a concave contour of the recessed portion spans a lateral axis of the recessed portion, and wherein the concave contour of the recessed portion of the patient support table has a radius of curvature of approximately 700 mm, and the convex contour of the bottom surface of the filler insert has a radius of curvature of approximately 700 mm.

8. The table insert according to claim 6, wherein filler insert comprises a foam core and a shell that comprises a para-aramid material.

9. The table insert according to claim 6, wherein the filler insert has an overall thickness of 20-100 mm.

10. The table insert according to claim 6, wherein the filler insert has an overall thickness in the range of 30-50 mm.

11. The table insert according to claim 6, wherein the filler insert has an overall thickness of approximately 40 mm.

12. The table insert according to claim 6, wherein the filler insert has an overall width in the range of 300 mm to 500 mm.

13. The table insert according to claim 6, wherein the filler insert has an overall length in the range of 400 mm to 600 mm.

14. A method of maintaining a flat surface on a patient support table when an insertable radio frequency (RF) head coil is not installed therein, comprising:
    maintaining a filler insert in a recessed portion of a patient support table;
    when a patient is to be scanned using an RF head coil, removing the filler insert and installing the RF head coil into the recessed portion of the patient support table;
    when the patient scan is complete, removing the RF head coil from the recessed portion of the patient support table and re-installing the filler insert into the recessed portion of the patient support table;
    wherein the recessed portion of the patient support table includes a central keying recess that is positioned approximately at a center of the recessed portion, and an anterior keying recess that is positioned along an anterior edge of the recessed portion, and wherein the filler insert includes an anterior keying feature that mates with the anterior keying recess and a central keying feature that mates with the central keying recess to align and secure the filler insert in place on the patient support table.

15. The method according to claim 14, wherein the recessed portion of the patient support table has a concave contour having a radius of curvature that is complementary to a convex contour radius of curvature of the bottom surface of the RF coil assembly and to a convex contour radius of curvature of the bottom surface of the filler insert wherein the radius of curvature of each of the recessed portion of the patient support table, the bottom surface of the RF head coil assembly, and the bottom surface of the filler insert is approximately 700 mm.

* * * * *